(12) United States Patent
Maiorino et al.

(10) Patent No.: US 8,056,599 B2
(45) Date of Patent: Nov. 15, 2011

(54) SYSTEM AND METHOD OF MAKING TAPERED LOOPED SUTURE

(75) Inventors: Nicholas Maiorino, Branford, CT (US); William R. Bowns, Ansonia, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 12/548,607

(22) Filed: Aug. 27, 2009

(65) Prior Publication Data

US 2010/0071833 A1    Mar. 25, 2010

Related U.S. Application Data

(60) Provisional application No. 61/099,594, filed on Sep. 24, 2008.

(51) Int. Cl.
 *B29C 65/02* (2006.01)
 *B32B 37/00* (2006.01)

(52) U.S. Cl. ........ 156/530; 156/494; 156/539; 156/257; 156/268; 156/73.2; 156/379.8

(58) Field of Classification Search ............... 156/494, 156/510, 539, 580.1, 257, 268, 73.2, 530, 156/379.8, 272.8; 606/144, 148, 167, 174, 606/228
 See application file for complete search history.

(56) References Cited

U.S. PATENT DOCUMENTS

| | | | |
|---|---|---|---|
| 3,513,848 A | 5/1970 | Winston et al. | |
| 3,657,056 A | 4/1972 | Winston et al. | |
| 3,874,963 A | 4/1975 | Barger | |
| 4,575,372 A * | 3/1986 | Gundersen | 623/1.41 |
| 4,662,068 A | 5/1987 | Polonsky | |
| 4,950,285 A | 8/1990 | Wilk | |
| 5,226,535 A | 7/1993 | Rosdhy et al. | |
| 5,259,846 A | 11/1993 | Granger et al. | |
| 5,383,905 A | 1/1995 | Golds et al. | |
| 5,403,331 A | 4/1995 | Chesterfield et al. | |
| 5,417,700 A | 5/1995 | Egan et al. | |
| 5,893,880 A | 4/1999 | Egan et al. | |
| 6,077,277 A | 6/2000 | Mollenauer et al. | |
| 6,089,438 A | 7/2000 | Suzuki | |
| 6,174,324 B1 | 1/2001 | Egan et al. | |
| 6,217,591 B1 | 4/2001 | Egan et al. | |
| 6,286,746 B1 | 9/2001 | Egan et al. | |
| 6,296,659 B1 | 10/2001 | Foerster | |
| 6,358,271 B1 | 3/2002 | Egan et al. | |
| 6,409,743 B1 | 6/2002 | Fenton, Jr. | |
| 6,488,690 B1 | 12/2002 | Morris et al. | |
| 6,669,705 B2 | 12/2003 | Westhaver et al. | |
| 6,767,426 B1 * | 7/2004 | Yamamoto | 156/270 |
| 7,090,111 B2 | 8/2006 | Egan et al. | |
| 7,429,266 B2 | 9/2008 | Bonutti et al. | |
| 7,533,791 B2 | 5/2009 | Steiner et al. | |
| 7,582,097 B2 | 9/2009 | McRury et al. | |
| 2004/0122451 A1 | 6/2004 | Wood | |
| 2005/0165448 A1 | 7/2005 | Egan et al. | |
| 2006/0025858 A1 | 2/2006 | Alameddine | |
| 2006/0259076 A1 | 11/2006 | Burkhart et al. | |
| 2009/0216269 A1 | 8/2009 | Harrington et al. | |
| 2009/0248070 A1 | 10/2009 | Kosa et al. | |
| 2009/0259251 A1 | 10/2009 | Cohen | |
| 2010/0101707 A1 * | 4/2010 | Maiorino et al. | 156/180 |

* cited by examiner

*Primary Examiner* — Linda L Gray

(57) ABSTRACT

A system for forming a looped suture having a tapered cut is provided. The system includes a base for selectively retaining a portion of thread, a clamping device for receiving a first end of the thread, a tensioning device for receiving a second end of the thread, a welding assembly configured to join a first and second section of the thread to form a loop, and a cutting assembly configured to form a tapered end on the first section of the thread.

21 Claims, 7 Drawing Sheets

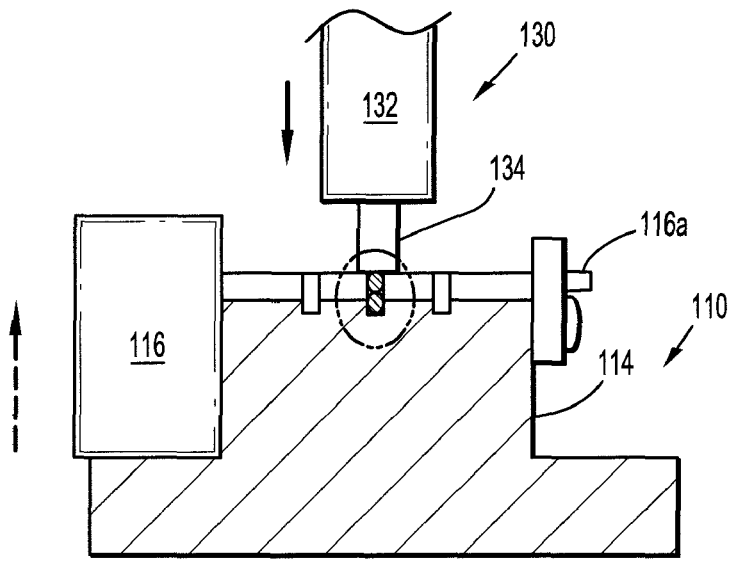
FIG. 3C
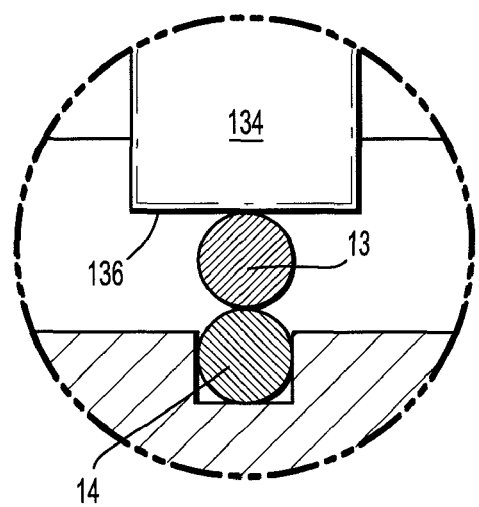 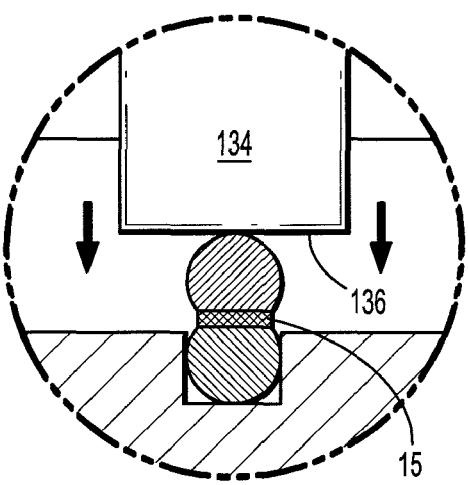
FIG. 4A   FIG. 4B

SYSTEM AND METHOD OF MAKING TAPERED LOOPED SUTURE

CROSS-REFERENCE TO RELATED APPLICATION

The present application claims benefit to and priority from U.S. Provisional Application Ser. No. 61/099,594, filed Sep. 24, 2008, the entire content of which is incorporated herein by reference.

BACKGROUND

1. Technical Field

The present disclosure relates to a method of forming a looped suture. More particularly, the present disclosure relates to a method of forming a looped suture having a tapered surface.

2. Background of Related Art

A method for forming a loop in a suture during a wound closing procedure (surgery) is known. It would be beneficial to have a system and method for more effectively forming a loop on a suture prior to engagement of tissue with the suture. It would be further beneficial if the system and method could form a tapered end on the loop.

SUMMARY

Accordingly, a system for forming a looped suture having a tapered surface is provided. The system includes a base for selectively retaining a portion of thread, a clamping device for receiving a first end of the thread, a tensioning device for receiving a second end of the thread, a welding assembly configured to join a first and second section of the thread to form a loop, and a cutting assembly configured to form a tapered end on the first section of the thread.

The base may include a suture nest, a pin retaining member, a pin, and a pin locking member. The base may include at least one channel for receiving at least a portion of the second section of the thread. The pin retaining member may be pivotally mounted to the base. The pin may be configured to receive a portion of the thread thereabout. The welding assembly of the system may be configured to weld using ultrasonic energy.

The cutting assembly of the system may be configured to cut using one of ultrasonic energy, blades and lasers. The cutting assembly may be configured to form a tapered end on the first section of thread that is generally linear or generally curved. The cutting assembly may be configured to form a tapered end on the first section of thread that is convex or concave. The cutting assembly may also be configured to form a tapered end on the first section of thread that is angled downwards towards a longitudinal axis of the elongate body. Furthermore, the cutting assembly may be configured to form a tapered end on the first section of thread that forms an angle of about zero degrees (0°) to about ninety degrees (90°), preferably, five degrees (5°) to about sixty degrees (60°), relative to a longitudinal axis of the elongated body. In addition, the cutting assembly may be configured to form a tapered end on the first section of thread that is suitable for penetrating tissue.

Further provided is a method of forming a loop in a suture thread. The method includes the steps of providing a loop forming system including, a base for securely retaining a thread to be formed, a welding assembly for forming a loop in the thread, and a cutting assembly for forming a taper on an end of the loop, securing a portion of the thread to the base such that a first section of the thread is maintained adjacent to a second section of the thread, approximating the welding assembly and the base towards each other, approximating the welding assembly and base away from each other, approximating the cutting assembly and the base towards each other, and cutting a tapered end on a proximal end of the first section of the thread, approximating the cutting assembly and base away from each other, and removing the formed suture from the base.

The loop forming system of the method may further include a clamping device for receiving a first end of a thread. The loop forming system may further include a tensioning device for tensioning a thread once the thread is retained in the base.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 3C is a cross-section front view of the loaded base of FIGS. 3A and 3B;

FIGS. 4A and 4B are enlarged views of FIG. 3C, with the suture in a pre-welded (FIG. 4A) and post-welded (FIG. 4B) configuration;

DETAILED DESCRIPTION

Figure 1A:
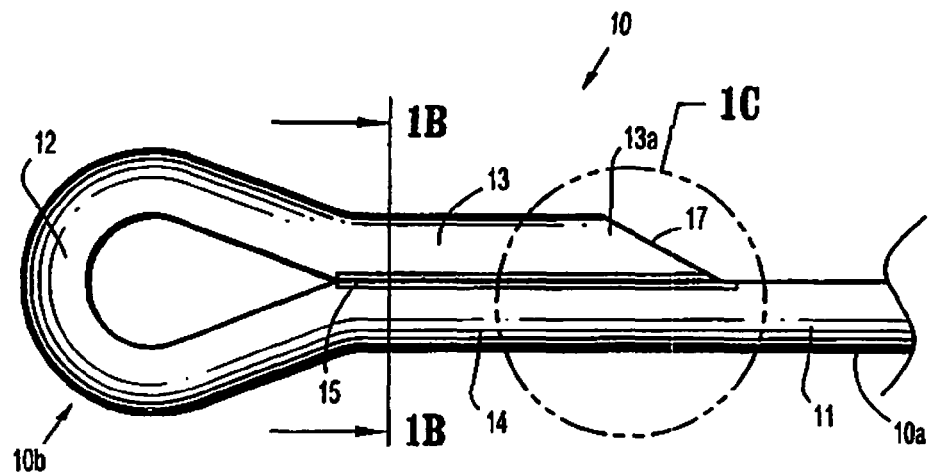
FIG. 1A is a side view of a looped suture including a tapered portion.

A method for forming a looped suture including a tapered surface is herein described. Referring initially to FIG. 1A, a looped suture formed in accordance with the method of the present disclosure is shown generally as looped suture 10. Suture 10 is formed from a monofilament thread 11; however, it is envisioned that suture 10 may be formed braided threads, multifilament threads and other surgical fibers. Although shown having a circular cross-sectional geometry, the cross-sectional geometry of thread 11 may be of any suitable shape, such as, round, elliptical, square, flat, octagonal, and rectangular. Thread 11 may be formed of degradable materials, non-degradable materials, and combinations thereof. Thread 11 may be formed using any technique within the purview of those skilled in the art, such as, for example, extrusion, molding and/or gel spinning.

Figure 1B:
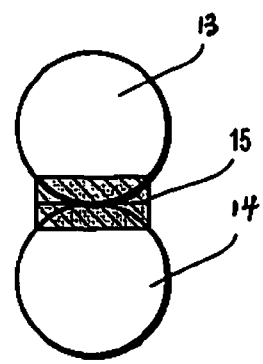
FIG. 1B is a cross-sectional end view of the looped suture of FIG. 1A, taken along line 1B-1B.

With reference to FIGS. 1A and 1B, looped suture 10 includes a loop 12 formed on a distal end 10b thereof. Loop 12 forms a substantially teardrop shape and may be formed of any size. A first section 13 of monofilament thread 11 overlays a second section 14 of thread 11 to form loop 12. The adjacent surfaces of first and second sections 13, 14 form a joined segment or joint 15. As shown, joined segment 15 extends beyond first section 13 of thread 11. In this manner, first and second sections 13, 14 of thread 11 are less likely to separate or peel away from each other as looped suture 10 is pulled through tissue (not shown).

As will be described in further detail below, first and second sections 13, 14 of thread 11 are welded together to form joined section 15. Energy is locally applied to first and second sections 13, 14 of thread 11 fusing sections 13, 14 together to form joined segment 15. Various types of energy may be applied to first and second sections 13, 14 to form joined segment 15, including, radio frequency (RF), ultrasonic, laser, electrical arc discharge, and thermal. Alternatively, first and second sections 13, 14 of thread 11 may be joined using glues, epoxies, solvents, or other adhesives.

Figure 1C:
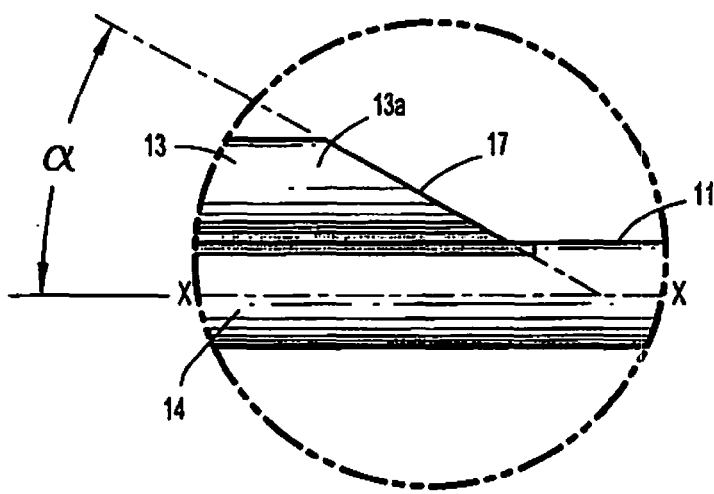
FIG. 1C is an enlarged side view of portion 1C of FIG. 1A.

With particular reference to FIG. 1C, a proximal end 13a of first section 13 is angled to form a tapered surface 17. Tapered surface 17 angles downwardly towards proximal end 10a of looped suture 10. Tapered surface 17 may form an angle α relative to a longitudinal axis "X" of second section 14, between zero degrees (0°) and ninety degrees (90°), and preferably between about five degrees (5°) to about sixty degrees (60°). Tapered surface 17 facilitates insertion of loop 12 into or through tissue. Tapered surface 17 may be formed prior to, during or following the joining of first and second sections 13, 14. In one embodiment, tapered surface 17 is formed such that joined segment 15 extends beyond first section 13 of thread 11. In this manner, tapered surface 17 forms a smooth transition with second section 14 of thread 11, thereby decreasing the likelihood that first and second sections 13, 14 might separate or peel away from each other as looped suture 10 is pulled through tissue.

Although shown having a substantially planar taper, tapered surface 17 may include any number of configurations. For example, tapered surface 17 may be beveled, may include a laterally and longitudinally concave taper, may include a laterally and longitudinally convex taper, or may include any combination thereof. Tapered surface 17 may be selected depending on the tissue being sutured and/or the depth loop 12 is desired to be received within the tissue.

A system for forming loop 12 on distal end 10b of looped suture 10 will now be described with reference to FIGS. 2A-6B, and is shown generally as system 100. System 100 includes a fixture member or base 110, a suture retaining member 120 (FIG. 3A), a suture tensioning member 125 (FIG. 3A), a welding assembly 130 (FIGS. 3A-3C), and a cutting assembly 140 (FIGS. 5A-6B).

Figure 2A:
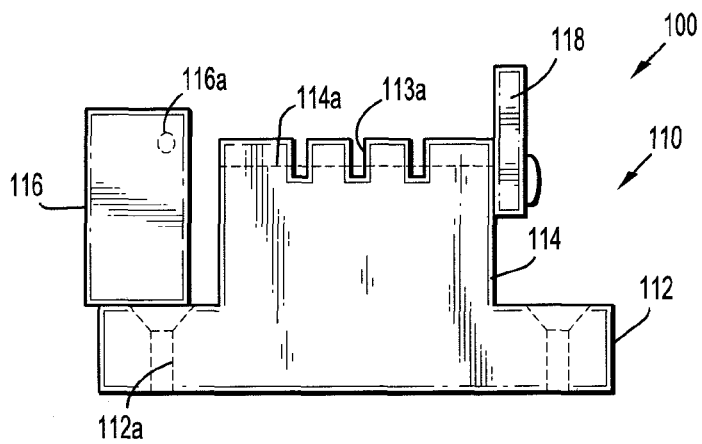
FIG. 2A is a front view of a base used in the tapered loop forming method of the present disclosure.
Figure 2B:
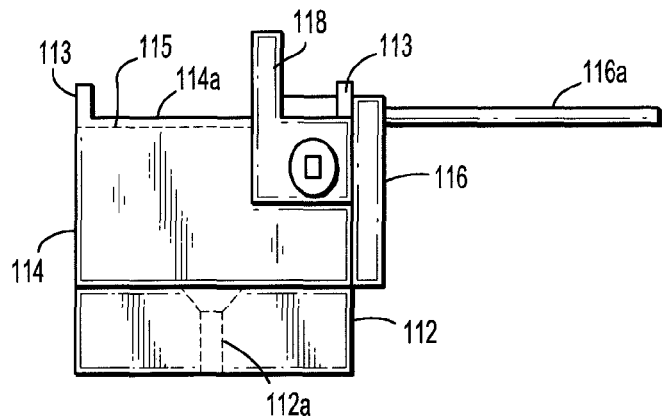
FIG. 2B is a side view of the base of FIG. 2A.
Figure 2C:
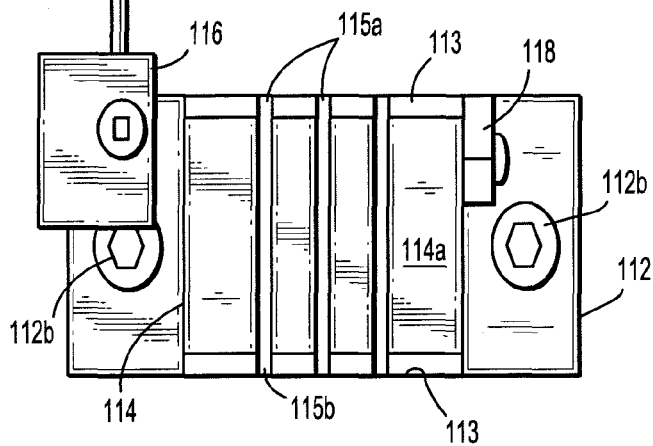
FIG. 2C is a top view of the base of FIGS. 2A and 2B.

Referring initially to FIGS. 2A-2C, base 110 includes a platform 112, a suture nest 114, a pin retaining member 116, a pin 116a extending from pin retaining member 116, and a pin lock 118. Platform 112 includes one or more openings 112a for securing base 110 to a workstation (not shown) using bolts 112b or other fixation means. As shown, suture nest 114 is integrally formed with platform 112. Alternatively, suture nest 114 may be releasably attached or securely affixed to platform 112. Nest 114 includes one or more channels 115 extending across a top surface 114a thereof. As will be described in further detail below, channels 115 are configured to partially receive a portion of suture thread 11, including second section 14 (FIG. 1). Nest 114 may further includes raised outer portions 113 extending along proximal and distal ends 115a, 115b of channels 115. Raised outer portions 113 include openings 113a configured to receive two lengths of suture thread 11, adjacent to or on top of one another. As shown, suture nest 114 includes three channels 115; however, it is envisioned that suture nest 115 may include one or more channels 115. In one embodiment, suture nest 115 may be formed without a channel. In this manner, the first and second portions of suture thread 11 would be received in opening 113a and are maintained adjacent to one another through the tension applied by suture tensioning means 125 (FIG. 3A).

Still referring to FIGS. 2A-2C, pin 116a extends from pin retaining member 116. Pin retaining member 116 is pivotally attached to platform 112 such that pin 116a may be selectively positioned and securely retained perpendicular to channels 115 along an end thereof (FIG. 3B). Pin lock 118 is pivotally attached to suture nest 114 and is configured to secure pin 116a in the perpendicular position adjacent proximal end 115a of channels 115. Alternatively, pin lock 118 may be integrally formed with suture nest 114. In another alternate embodiment, pin retaining member 116 may be releasably attached or securely affixed to platform 112. The diameter of pin 116a may be varied depending on the desired size of loop 12.

Figure 3A:
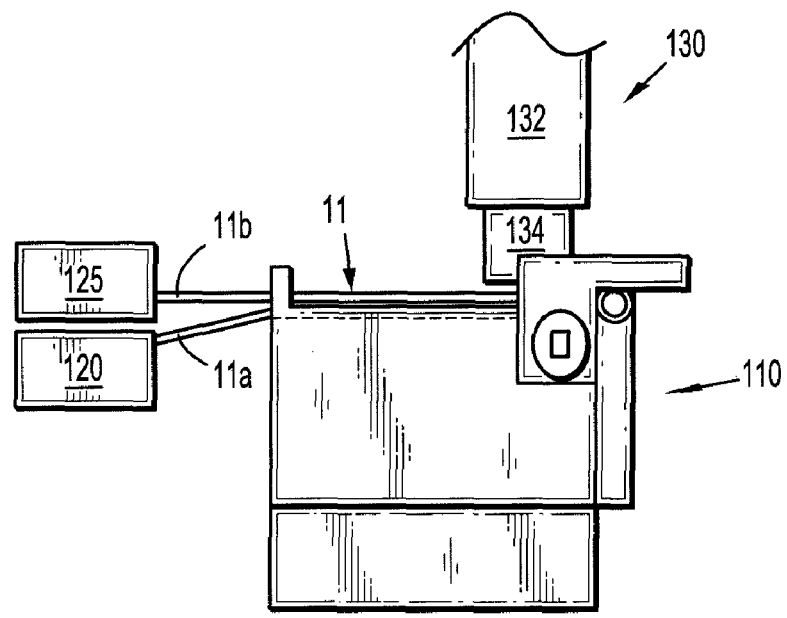
FIG. 3A is a side view of the base of FIGS. 2A-2C loaded with a suture and including a welding assembly, a suture retaining assembly and a suture tensioning assembly.
Figure 3B:
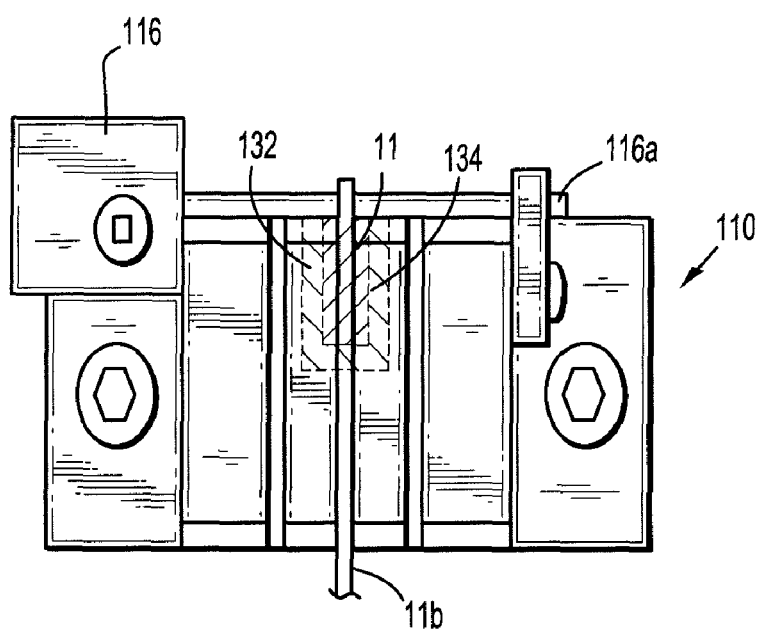
FIG. 3B is a top view of the loaded base of FIG. 3A.
Figure 5A:
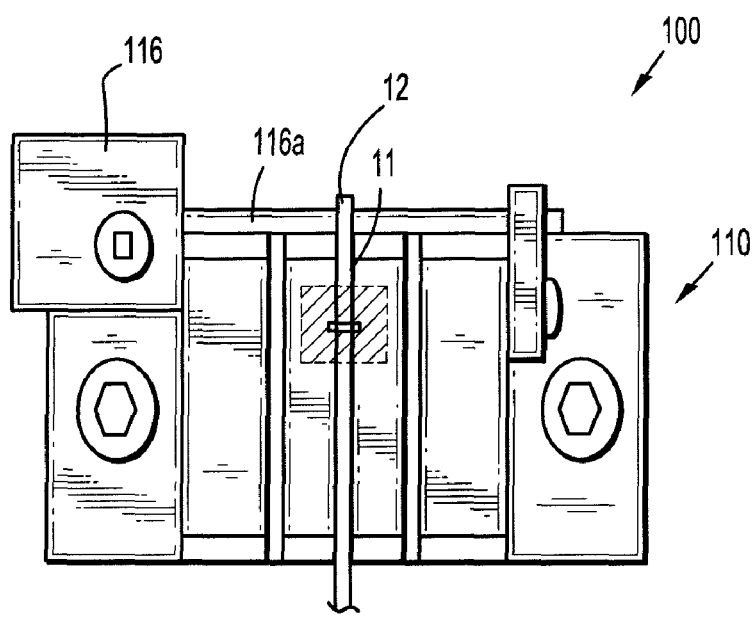
FIG. 5A is a top view of the loaded base of FIGS. 3A-3C, post-welding and prior to the tapered cut being formed.
Figure 5B:
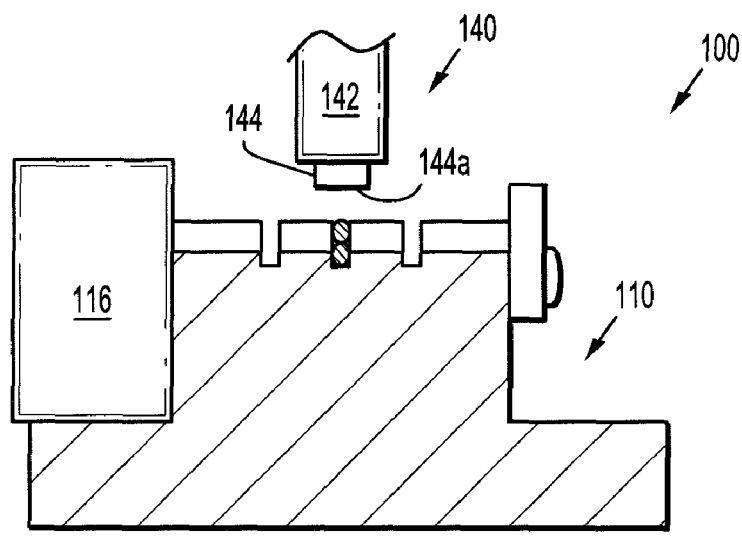
FIG. 5B is a cross-sectional front view of the loaded base of FIG. 5A.
Figure 5C:
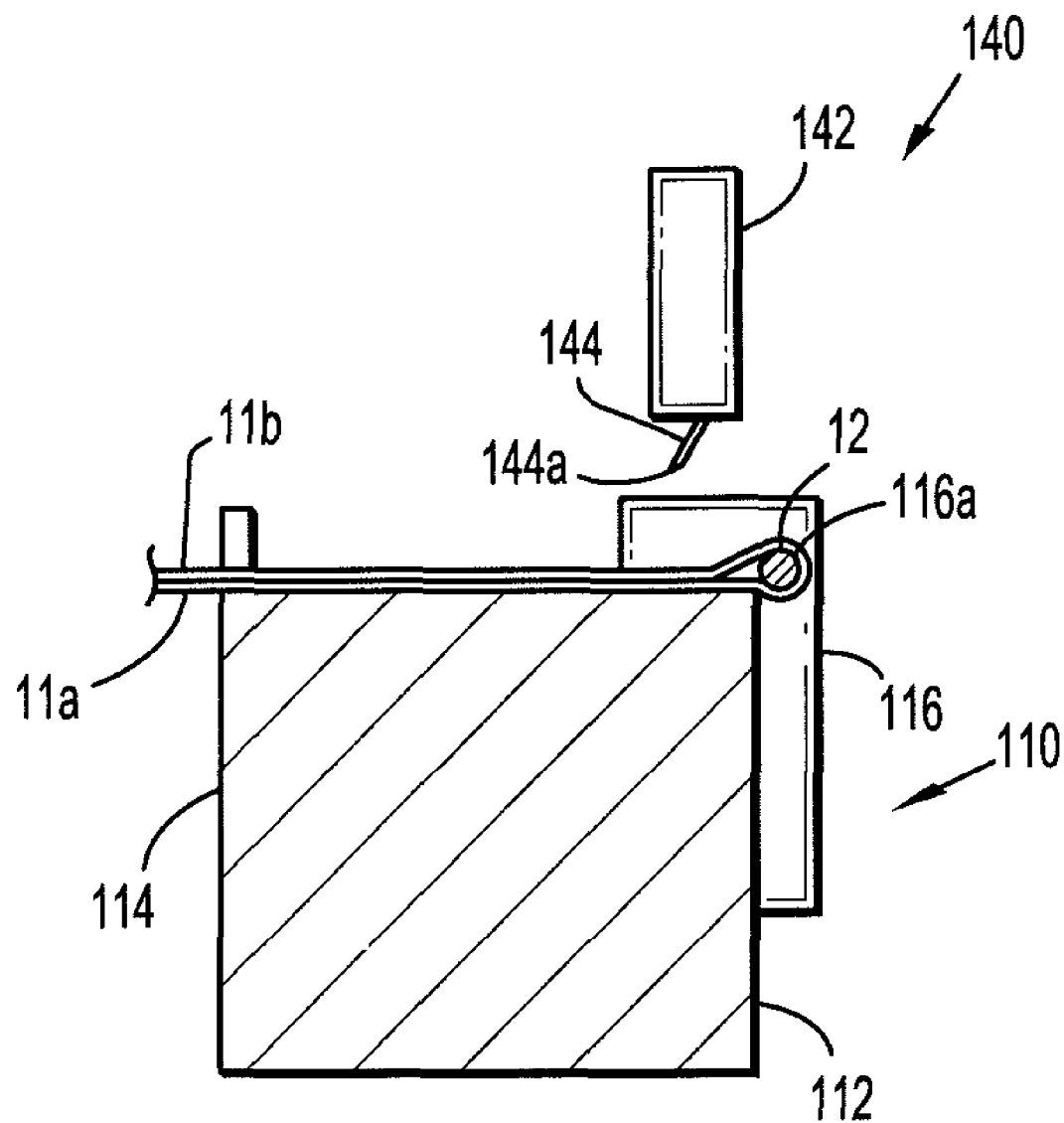
FIG. 5C is a cross-sectional side view of the loaded base of FIGS. 5A and 5B.

Turning briefly to FIG. 3A, as discussed above, system 100 also includes a suture retaining means 120 and a suture tensioning means 125. Suture retaining means 120 may include a clamp or other device configured to retain a proximal end 11a of suture thread 11. Suture tensioning means 125 may include a hydraulic or pneumatic tensioning spring, electrical cylinder or other tensioning device configured to receive a distal end 11b of suture thread 11 and to apply tension to suture thread 11 once thread 11 has been secured to suture nest 114. Suture retaining means 120 and suture tensioning means 125 are positioned adjacent distal end 115b of channel 115 to securely receive respective proximal and distal ends 11a, 11b of suture thread 11 during the forming of loop 12.

With reference to FIGS. 3A-4B, welding assembly 130 includes an ultrasonic device 132 operably connected to a generator (not shown) for ultrasonically vibrating a die 134 extending from ultrasonic device 132. Die 134 defines a substantially flat suture contacting portion 136. In an alternative embodiment, die 134 may include a portion 136 configured to contour first section 13 of suture thread 11. Thus, suture contacting portion 136 may include a concave, convex or beveled surface to correspond with a suture thread having a convex, concave or beveled profile. In one embodiment, welding assembly 130 is operatively mounted on a press assembly (not shown) for approximating die 134 of welding assembly 130 towards and away from base 110. Alternatively, welding assembly 130 may be securely mounted relative to base 110 and base 110 may be raised and lowered to approximate base 110 towards and away from die 134.

Turning now to FIGS. 5A-6B, cutting assembly 140 includes an ultrasonic device 142 operably connected to a generator (not shown) for ultrasonically vibrating a blade 144 extending from ultrasonic device 142. The generator for ultrasonically vibrating die 134 may be the same or a different generator as is operatively connected to ultrasonic device 142 for ultrasonically vibrating blade 144. In one embodiment, blade 144 defines a substantially flat cutting surface 144a; however, it is envisioned that blade 144 may include a cutting surface of alternative configurations. Blade 144 may be configured to form a concave, convex, beveled or otherwise configured taper 17 on looped suture 10. Although the following discussion will relate to a cutting assembly that includes an ultrasonic device 142, it is envisioned that cutting assembly 140 may be used without ultrasonically vibrating blade 144. In this manner, blade 144 may be operably connected to a heater or other apparatus for effecting cutting of suture thread 11. In yet another embodiment, taper 17 on looped suture 10 may be cut using a laser.

Still referring to FIGS. 5A-6B, in one embodiment, cutting assembly 140 is securely mounted relative to base 144 such that cutting assembly 140 is maintained stationary as base 110 is approximated towards and away from blade 144. In an alternative embodiment, cutting assembly 140 is selectively positioned relative to base 110, such that cutting assembly 140 moved relative to base 110. In either embodiment, at least one of cutting assembly 140 and base 110 is configured to move laterally with respect to the other and approximate towards the other. When cutting assembly 140 is maintained stationary, base 110 is configured to move laterally, in the direction of arrow A1 (FIG. 6B) and towards cutting assembly 140, in the direction of arrow A2. When base 110 is maintained stationary, cutting assembly 140 is configured to move laterally, in the direction of arrow B1 and towards base 110, in the direction of arrow A2. Movement of base 110 and/or cutting assembly 140 may be computer controlled or may be effected manually.

The method of forming looped suture 10 utilizing system 100 will now be described with reference to FIGS. 3A-6B. Referring initially to FIG. 3A, a proximal end 11a of thread 11 is securely locked in a clamp 120. Second section 14 of thread 11 is then positioned within a channel 115 of nest 114. Thread 11 is next wrapped around pin 116a before first section 13 of thread 11 is placed on top of or adjacent second section 14. A distal end 11b of thread 11 is then received in tension cylinder 125. Tensioning cylinder 125 is then activated to tension thread 11 within base 110. To prevent stretching of thread 11 during forming of looped suture 10, and thereby ensuring consistency and integrity of thread 11, thread 11 may be formed of a pre-stretched material.

With particular reference now to FIGS. 3C-4B, once first and second sections 13, 14 are positioned adjacent one another, welding assembly 130 is approximated towards suture nest 114. Alternatively, suture nest 114 may be approximated towards welding assembly 130. As welding assembly 130 nears suture nest 114, first section 13 of suture thread 11 is received within channel 136 of die 134 until first section 13 engages suture contacting portion 136a of channel 136 (FIG. 4A). Ultrasonic device 132 may be activated at any point during this process to ultrasonically vibrate die 134. The downward pressure exerted on first and second sections 13, 14 of thread 11 from the continued approximation of die 134 towards nest 114 (FIG. 4B), in combination with ultrasonic vibration of die 134, causes contacting portions of first and second sections 13, 14 to locally heat, and, in some instances, the contacting portions may begin to melt. Application of ultrasonic energy to sections 13, 14 creates joined section 15.

Once first and second sections 13, 14 are fused to create joined section 15, welding assembly 130 may be approximated away from suture nest 114. With looped suture 10 remaining secured to base 110, welding assembly 130 may then be replaced or exchanged for cutting assembly 140 to complete the tapered cutting of proximal end 13a of first section 13. Alternatively, looped suture 10 may be removed from base 110 and affixed to a separate mount (not shown) to complete the taper forming process.

Figure 6A:
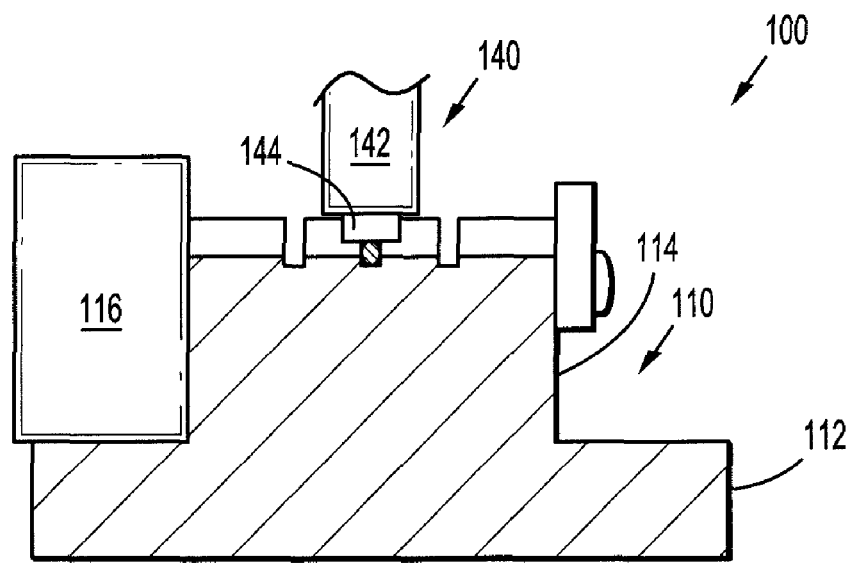
FIG. 6A is a cross-sectional front view of the loaded base of FIGS. 5A-5C, post-welding and post-cutting of the suture.
Figure 6B:
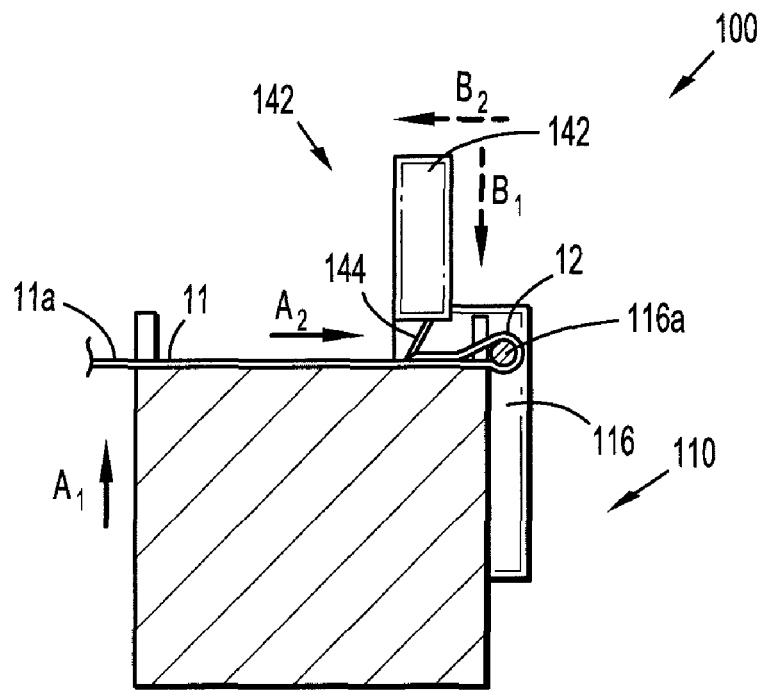
FIG. 6B is a cross-sectional side view of the loaded base of FIG. 6A.

With reference now to FIGS. 5A-6B, once cutting assembly 130 is properly positioned in relation to base 110, base 110 is approximated towards cutting assembly 140. Alternatively, cutting assembly 140 may be approximated towards base 110. Ultrasonic device 142 may be activated at any time prior to or during approximation of cutting assembly 140 towards base 110. With particular reference to FIG. 6B, the travel of base 110 in relation to cutting assembly 140 includes an upward movement, as indicated by arrow $A_1$ and lateral movement, as indicated by arrow $A_2$. In an alternative embodiment, cutting assembly 140 is moved in a downward movement, as indicated by arrow $B_1$ and a lateral movement, as indicated by arrow $B_2$. The rate at which base 110 moves relative to cutting assembly 140 may be varied depending on the desired configuration of tapered surface 17 (FIG. 1C). In this manner, when the lateral movement is increased relative to the up/down movement, tapered surface 17 defines an angle $\alpha$ (FIG. 1C) of a lesser degree. Conversely, when the lateral movement of is decreased relative to the up/down movement, angle $\alpha$ of tapered surface 17 is increased. In either embodiment, cutting assembly 130 and base 110 are approximated toward one another until blade 144 completely severs first section 13 of thread 11. Distal end 11b of thread 11 is then pulled away by tension cylinder 125.

Cutting assembly 130 and base 110 are then approximated away from each other and looped suture 10 is removed from pin 116a. Suture 10 may include flash or debris (not shown) formed during the welding and/or cutting process. The flash may need to be removed before looped suture 10 may be used.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that system 100 may include more than one welding assembly 130 and a corresponding number of cutting assemblies 140 to produce more than one suture 10 per activation. It is further envisioned that system 100 may include a separate base for maintaining suture 10 during the cutting process.

What is claimed is:

1. A system for forming a looped suture having a tapered cut, the system comprising:
   a base for selectively retaining a first section and a second section of a thread;
   a clamping device for receiving a first end of the thread;
   a tensioning device for receiving a second end of the thread;
   a welding assembly configured to join the first section of the thread and the second section of the thread to form a loop; and
   a cutting assembly configured to form a tapered end on the first section of the thread, wherein the base is configured to retain the thread in a fixed position relative to the base throughout the joining of the first and second sections of the thread and the cutting of the tapered end.

2. The system of claim 1, wherein the base includes a suture nest, a pin retaining member, a pin, and a pin locking member.

3. The system of claim 2, wherein the pin retaining member is pivotally mounted to the base.

4. The system of claim 2, wherein the pin is configured to receive a portion of the thread thereabout.

5. The system of claim 1, wherein the base includes at least one channel for receiving at least the second section of the thread.

6. The system of claim 1, wherein the cutting assembly is configured to cut using one of ultrasonic energy, blades, and lasers.

7. The system of claim 1, wherein the welding assembly is configured to weld using ultrasonic energy.

8. The system of claim 1, wherein the cutting assembly is configured to form a tapered end on the first section of thread that is generally linear.

9. The system of claim 1, wherein the cutting assembly is configured to form a tapered end on the first section of thread that is generally curved.

10. The system of claim 9, wherein the cutting assembly is configured to form a tapered end on the first section of thread that is convex.

11. The system of claim 9, wherein the cutting assembly is configured to form a tapered end on the first section of thread that is concave.

12. The system of claim 1, wherein the cutting assembly is configured to form a tapered end on the first section of thread that is angled downwards towards a longitudinal axis of the thread.

13. The system of claim 1, wherein the cutting assembly is configured to form a tapered end on the first section of thread that is suitable for penetrating tissue.

14. The system of claim 1, wherein the cutting assembly is configured to form a tapered end on the first section of thread that forms an angle of about zero degrees (0°) to about ninety degrees (90°) relative to the a longitudinal axis of the thread.

15. The system of claim 1, wherein the cutting assembly is configured to form a tapered end on the first section of thread that forms an angle of about five degrees (5°) to about thirty degrees (30°).

16. The system of claim 1, wherein the base is configured to retain the first section of the thread adjacent to the second section of thread.

17. The system of claim 1, wherein at least one of the base and the welding assembly are approximated towards the other of the welding assembly and the base to join the first and second sections of the thread.

18. The system of claim 1, wherein at least one of the base and the cutting assembly are approximated towards the other of the cutting assembly and the base to form the tapered end on the first section of the thread.

19. A system for forming a looped suture having a tapered cut, the system comprising:
   a base for selectively retaining a first longitudinal section of a thread adjacent a second longitudinal section of the thread;
   a clamping device for receiving a first end of the thread;
   a tensioning device for receiving a second end of the thread;
   a welding assembly configured to join the first section of the thread and the second section of the thread to form a loop; and
   a cutting assembly configured to form a tapered end on the first section of the thread.

20. A system for forming a looped suture having a tapered cut, the system comprising:
   a base for retaining a length of thread in a fixed position relative to the base throughout a loop forming process;
   a clamping device for receiving a first end of the thread;
   a tensioning device for receiving a second end of the thread;
   a welding assembly configured to join the first section of the thread and the second section of the thread to form a loop; and
   a cutting assembly configured to form a tapered end on the first section of the thread.

21. The system according to claim 20, wherein the loop forming process includes welding and cutting the thread.

* * * * *